(12) United States Patent
Lim et al.

(10) Patent No.: US 8,460,397 B2
(45) Date of Patent: Jun. 11, 2013

(54) OXIDATIVE DYEING COMPOSITIONS COMPRISING AN 1-HEXYL/HEPTYL-4,5-DIAMINOPYRAZOLE AND A PYRIDINE AND DERIVATIVES THEREOF

(75) Inventors: Muill Lim, Chuncheon-Si (KR); Bryan Patrick Murphy, Loveland, OH (US); Margaret Ann Popp, West Chester, OH (US); Richard Matthew Charles Sutton, Cincinnati, OH (US); Guiru Zhang, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/398,201

(22) Filed: Feb. 16, 2012

(65) Prior Publication Data

US 2012/0210526 A1    Aug. 23, 2012

Related U.S. Application Data

(60) Provisional application No. 61/445,308, filed on Feb. 22, 2011.

(51) Int. Cl.
*A61Q 5/10* (2006.01)
*C07D 231/00* (2006.01)
*C07D 213/00* (2006.01)

(52) U.S. Cl.
USPC ............... 8/405; 8/406; 8/408; 8/409; 8/431; 8/435; 8/568; 8/573; 8/690; 548/371.4; 546/257

(58) Field of Classification Search
USPC ............ 8/405, 406, 408, 409, 431, 435, 568, 8/573, 690; 546/257; 548/371.4
See application file for complete search history.

(56) References Cited

U.S. PATENT DOCUMENTS 5,061,289 A    10/1991 Clausen (Continued)

FOREIGN PATENT DOCUMENTS

CA    2646867 A1    3/2009

(Continued)

OTHER PUBLICATIONS

STIC Search Report dated Jun. 22, 2012.*

*Primary Examiner* — Eisa Elhilo
(74) *Attorney, Agent, or Firm* — James T. Fondriest; Carl J. Roof

(57) ABSTRACT

A composition for the oxidative dyeing of keratin fibers, in particular human keratin fibers, comprising (A) a 1-hexyl/heptyl-4,5-diaminopyrazole compound of the general formula (I), its physiologically compatible water-soluble salt, or mixtures thereof; (B) a pyridine compound of the general formula (II), its physiologically compatible water-soluble salt, or mixtures thereof; and (C) an oxidizing agent.

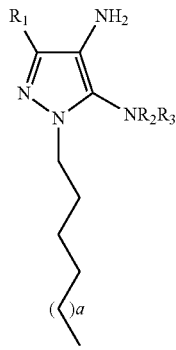

(I)

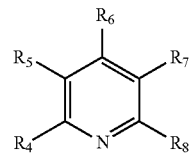

(II)

wherein $R_1$, $R_2$, $R_3$, $R_4$, $R_5$, $R_6$, $R_7$ and $R_8$ are as defined herein and a=1 or 2.

17 Claims, 1 Drawing Sheet

U.S. PATENT DOCUMENTS

| | | | |
|---|---|---|---|
| 5,380,340 A | 1/1995 | Neunhoeffer |
| 5,430,159 A | 7/1995 | Neunhoeffer |
| 5,534,267 A | 7/1996 | Neunhoeffer |
| 5,663,366 A | 9/1997 | Neunhoeffer |
| 5,718,731 A | 2/1998 | Loewe |
| 5,752,983 A | 5/1998 | Audousset |
| 5,766,576 A | 6/1998 | Loewe |
| 5,769,902 A | 6/1998 | Samain |
| 5,785,717 A | 7/1998 | Maubru |
| 5,865,855 A | 2/1999 | Doehling |
| 5,931,973 A | 8/1999 | Malle |
| 6,090,162 A | 7/2000 | Maubru |
| 6,118,008 A | 9/2000 | Malle |
| 6,338,741 B1 | 1/2002 | Vidal |
| 6,379,396 B1 | 4/2002 | Audousset |
| 6,452,019 B1 | 9/2002 | Cook |
| 6,503,282 B1 | 1/2003 | Braun |
| 6,554,871 B2 | 4/2003 | Braun |
| 6,600,050 B2 | 7/2003 | Chassot |
| 6,645,258 B2 | 11/2003 | Vidal |
| 6,660,046 B1 | 12/2003 | Terranova |
| 6,716,257 B2 | 4/2004 | Goettel |
| 6,740,127 B2 | 5/2004 | Friess |
| 6,780,203 B1 | 8/2004 | Maubru |
| 6,793,687 B2 | 9/2004 | Javet |
| 6,855,827 B2 | 2/2005 | Vidal |
| 6,887,280 B2 | 5/2005 | Lim |
| 6,905,522 B2 | 6/2005 | Kravtchenko |
| 6,939,382 B2 | 9/2005 | Fessmann |
| 7,004,979 B2 | 2/2006 | Kravtchenko |
| 7,014,663 B2 | 3/2006 | Fessmann |
| 7,018,426 B2 | 3/2006 | Javet |
| 7,056,354 B2 | 6/2006 | Fessmann |
| 7,070,629 B2 | 7/2006 | Kravtchenko |
| 7,091,350 B2 | 8/2006 | Fessmann |
| 7,153,330 B2 | 12/2006 | Cotteret |
| 7,195,649 B2 | 3/2007 | Goettel |
| 7,204,861 B2 | 4/2007 | Marsh |
| 7,226,487 B2 | 6/2007 | Lim et al. |
| 7,250,063 B2 | 7/2007 | Fessmann |
| 7,285,136 B2 | 10/2007 | Fessmann |
| 7,285,137 B2 | 10/2007 | Vidal |
| 7,300,469 B2 | 11/2007 | Fessmann |
| 7,491,244 B2 | 2/2009 | Chassot |
| 7,597,720 B2 | 10/2009 | Marsh |
| 7,927,381 B2 | 4/2011 | Hercouet |
| 7,951,209 B2 | 5/2011 | Cotteret |
| 2003/0000027 A1 | 1/2003 | Hoeffkes |
| 2003/0106167 A1 | 6/2003 | Rose |
| 2004/0216242 A1 | 11/2004 | Kravtchenko |
| 2005/0015893 A1* | 1/2005 | Fessmann et al. ............. 8/405 |
| 2006/0183781 A1 | 8/2006 | Goettel |
| 2007/0033742 A1 | 2/2007 | Gottel |
| 2007/0037987 A1 | 2/2007 | Chamberlin |
| 2007/0050924 A1 | 3/2007 | Cotteret |
| 2007/0209124 A1 | 9/2007 | Bureiko |
| 2012/0210519 A1 | 8/2012 | Lim |
| 2012/0210520 A1 | 8/2012 | Lim |
| 2012/0210521 A1 | 8/2012 | Lim |
| 2012/0210522 A1 | 8/2012 | Lim |
| 2012/0210524 A1 | 8/2012 | Lim |
| 2012/0210525 A1 | 8/2012 | Lim |

FOREIGN PATENT DOCUMENTS

| | | | |
|---|---|---|---|
| DE | 3432983 A1 | 4/1985 |
| DE | 19619112 A1 | 11/1997 |
| DE | 10037158 A1 | 2/2002 |
| DE | 20017640 U1 | 2/2002 |
| EP | 0663204 A1 | 7/1995 |
| EP | 1166748 A2 | 1/2002 |
| EP | 0873109 B1 | 2/2004 |
| EP | 1405628 A1 | 4/2004 |
| EP | 1166749 B1 | 10/2005 |
| EP | 1488783 B1 | 11/2006 |
| EP | 1787631 A1 | 5/2007 |
| EP | 1787632 A1 | 5/2007 |
| EP | 1795178 A2 | 6/2007 |
| EP | 1795179 A1 | 6/2007 |
| EP | 1797863 A1 | 6/2007 |
| EP | 1985282 A2 | 10/2008 |
| FR | 2604622 A1 | 4/1988 |
| FR | 2831055 A1 | 4/2003 |
| WO | 0147475 A2 | 7/2001 |
| WO | 0209662 A2 | 2/2002 |
| WO | 02055500 A1 | 7/2002 |
| WO | 02083090 A2 | 10/2002 |
| WO | 2004024109 A1 | 3/2004 |
| WO | 2005023209 A1 | 3/2005 |
| WO | 2005123019 A1 | 12/2005 |
| WO | 2006108458 A1 | 10/2006 |
| WO | 2008047210 A2 | 4/2008 |
| WO | 2009077390 A2 | 6/2009 |

* cited by examiner

OXIDATIVE DYEING COMPOSITIONS COMPRISING AN 1-HEXYL/HEPTYL-4,5-DIAMINOPYRAZOLE AND A PYRIDINE AND DERIVATIVES THEREOF

CROSS REFERENCE TO RELATED APPLICATION(S)

This application claims the benefit of U.S. Provisional Application No. 61/445,308, filed on Feb. 22, 2011.

FIELD OF THE INVENTION

The present invention relates to a composition for the oxidative dyeing of keratin fibers, in particular human keratin fibers, comprising (A) a 1-hexyl/heptyl-4,5-diaminopyrazole compound as defined in formula (I) hereafter, its physiologically compatible water-soluble salt, or mixtures thereof, (B) a pyridine compound of the general formula (II) as defined hereafter, its physiologically compatible water-soluble salt, or mixtures thereof, and (C) an oxidizing agent.

BACKGROUND OF THE INVENTION

The oxidative dyeing of hair is one of the most extensively used methods to color hair. In this process oxidative hair coloring precursors are used in combination with an oxidizing agent, commonly a peroxy oxidizing agent. The precursors are generally small molecules capable of diffusing into hair, generally comprising primary intermediates and couplers. A wide variety of primary intermediates and couplers have been employed in such oxidative hair coloring compositions. Selections of specific combinations of couplers and primary intermediates allow reaching the desired nuance of hair color.

Besides providing the desired color, the dye precursors used for oxidative hair dyeing have to also meet some additional requirements. Indeed, the combination of couplers and primary intermediates used should deliver the desired intensity together with good wash and bleeding fastness and be acceptable from a toxicological and dermatological point of view.

Pyrazole compounds have been disclosed as oxidative dye precursors. A colorant for keratin fibers comprising a pyrazole derivative (I), a m-aminophenol derivative (II) and a pyridine derivative (III) is known. See for example EP 1166748A2.

The compositions of the prior art comprising pyrazole compounds are not satisfactory especially in terms of intensity, wash fastness and bleeding.

Furthermore, these disclosures do not disclose an example with a selection of a C6/C7 straight chain alkyl substituent on the N-1 position of a 4,5-diaminopyrazole.

The invention provides novel dye compositions that overcome known drawbacks of pyrazole compounds. In particular the invention provides good hair color intensity together with good wash and bleeding fastness. Indeed, it has surprisingly been found that the modification of the pyrazole ring system on the N-1 position by a C6/C7 straight alkyl chain combined with pyridine couplers provides excellent properties of resistance to the various treatments which keratinous fibers may undergo.

SUMMARY OF THE INVENTION

The present invention relates to a composition for the oxidative dyeing of keratin fibers, in particular human keratin fibers comprising (A) a 1-hexyl/heptyl-4,5-diaminopyrazole compound of the general formula (I), its physiologically compatible water-soluble salt, or mixtures thereof; (B) a pyridine compound of the general formula (II), its physiologically compatible water-soluble salt, or mixtures thereof; and (C) an oxidizing agent.

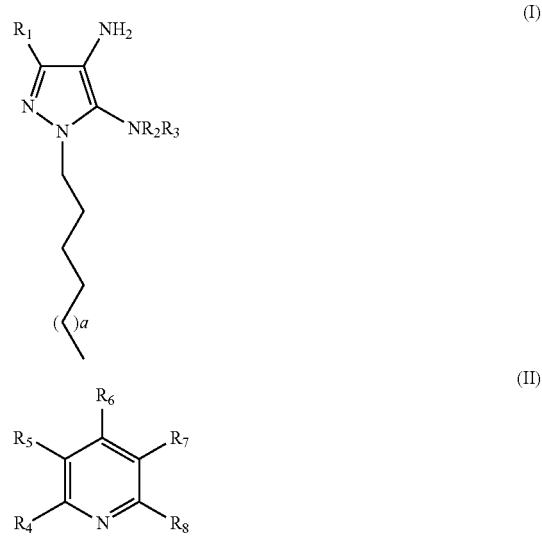

wherein $R_1$, $R_2$, $R_3$, $R_4$, $R_5$, $R_6$, $R_7$ and $R_8$ are as defined in the claims and a=1 or 2.

The present invention also relates to a method of dyeing hair comprising the steps of applying this composition to hair, and to a kit comprising: (i) a tint component comprising at least (a) a 1-hexyl/heptyl-4,5-diamino pyrazole compound of the general formula (I), its physiologically compatible water-soluble salt, or mixtures thereof, (b) a pyridine compound of the general formula (II), its physiologically compatible water-soluble salt, or mixtures thereof, and (ii) a developer component comprising (c) an oxidizing agent.

DETAILED DESCRIPTION OF THE INVENTION

Definitions

Figure 1:
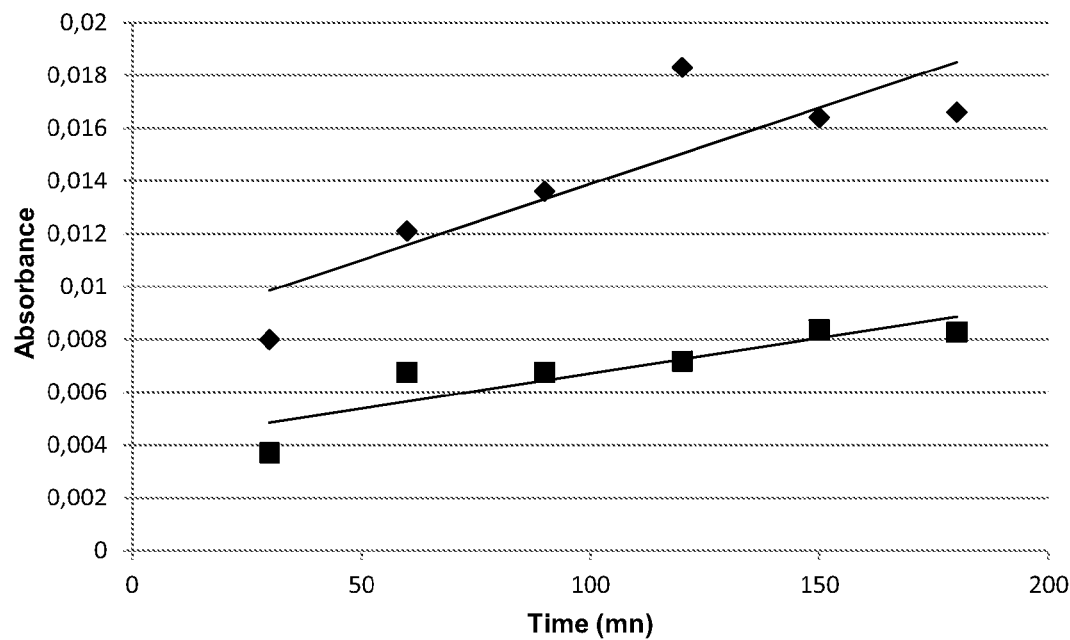
FIG. 1 shows a graph demonstrating the Solution Diffusion Testing results of a 1-pentyl- and 1-hexyl-4,5-diamino pyrazole with 2,6-dimethoxypyridine-3,5-diamine (compound of formula (II.2)).

As used herein, the term "composition for the oxidative dyeing of keratin fibers" means a ready-to-use composition in a suitable carrier medium for dyeing keratin fibers, in particular human hair, comprising oxidative dye precursors (primary intermediates and couplers) and an oxidizing agent. These compositions can typically be the result of a mixture of two compositions namely a tint component comprising the dye precursors and usually an alkalizing agent such as ammonia and/or monoethanolamine and a developer component comprising the oxidizing agent.

As used herein, the term "keratin" refers to a scleroprotein found in epidermal tissues and modified into hard structures such as horns, hair, and nails. As used herein, the term "hair" refers to keratinous fibers on a living, e.g. a person, or non-living body, e.g. in a wig, hairpiece, or other aggregation of non-living keratinous fibers. Mammalian, preferably human, hair is preferred. Notably, hair, wool, fur, and other keratinous fibers are suitable substrates for coloring by the compounds and compositions described herein.

As used herein, the term "dye precursors" refers to compounds that may be used in the composition to act as primary intermediates, couplers, or both, in order to provide color to keratinous fibers.

It is to be understood that when this development refers to a particular structure, all of the reasonable additional tautomeric structures are included. In the art, tautomeric structures are frequently represented by one single structure and the invention follows this general practice.

Pyrazole Compound

The 1-hexyl/heptyl-4,5-diaminopyrazole compound of the invention is of the general formula (I), its physiologically compatible water-soluble salt, or mixtures thereof:

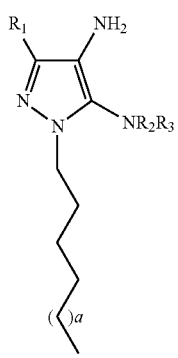

(I)

wherein a is equal to one or two;
wherein $R_1$ is selected from the group consisting of:
(a) C-linked substituents selected from the group consisting of:
  (i) substituted or unsubstituted, straight or branched or cyclic, saturated or unsaturated, aliphatic or heteroaliphatic substituents, in particular alkyl or hydroxy substituted alkyl,
  (ii) substituted or unsubstituted, mono- or poly-unsaturated aromatic or heteroaromatic substituents, in particular aryl or heteroaryl,
wherein said C-linked substituents comprise from 1 to 6 carbon atoms and from 0 to 5 heteroatoms selected from the group consisting of 0, F, N, P and Si;
(b) S-linked substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
(c) O-linked substituents selected from the group consisting of $OA^1$, $ONA^1A^2$;
(d) N-linked substituents selected from the group consisting of $NA^1A^2$; $(NA^1A^2A^3)^+$, $NA^1SA^2$, $NO_2$; $NA^1A^2$;
(e) halogens selected from the group consisting of F, Cl, Br, and I; and
(f) hydrogen;
wherein $A^1$, $A^2$, and $A^3$ are independently selected from the group consisting of hydrogen; substituted or unsubstituted, straight or branched or cyclic, saturated or unsaturated, aliphatic or heteroaliphatic or aromatic or heteroaromatic substituents, preferably substituted or unsubstituted alkyl, or $A^1$ and $A^2$ together with nitrogen atoms to which they are bound form a ring; wherein said substituents or ring comprise from 1 to 6 carbon atoms and from 0 to 5 heteroatoms selected from the group consisting of O, S, N, P, and Si;

$R_2$ and $R_3$ are selected independently of each other from the group consisting of a hydrogen atom; a C1-C6 alkyl substituent; a trifluoromethyl substituent; a C1-C6 aminoalkyl substituent; a C1-C6 hydroxyalkyl substituent; C1-C6 an alkoxyalkyl substituent.

Suitable salts of formula (I) are for example chlorides, bromides, sulfates, malates, tartrates, lactates and acetates. Of particular interest is the hemisulfate salt, which can provide a better stability during storage than other salts such as chloride or sulfate.

In a preferred embodiment the 1-hexyl/heptyl-4,5-diaminopyrazole compound (I) is a compound with formula (I.1):

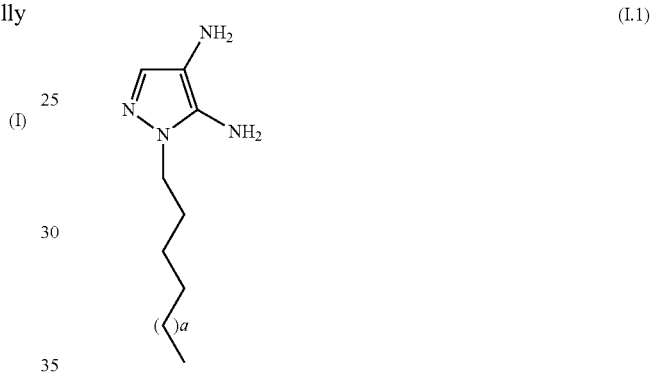

(I.1)

wherein a is equal to one or two.

The 1-hexyl/heptyl-4,5-diaminopyrazole compounds of formula (I) are combined with a pyridine compound of formula (II) in order to provide a resulting hair color with excellent washfastness, bleeding fastness, and intensity.

Pyridine Compound

The pyridine compound of the invention is according to the general formula (II) below, or a physiologically compatible water-soluble salt:

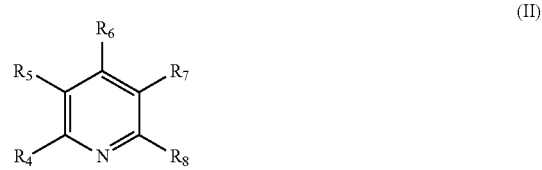

(II)

wherein $R_4$, $R_5$, $R_6$, $R_7$ and $R_8$ are substituents selected independently of each other from the group consisting of:
(a) C-linked substituents selected from the group consisting of:
  (i) substituted or unsubstituted, straight or branched or cyclic, saturated or unsaturated, aliphatic or heteroaliphatic substituents, in particular alkyl or hydroxy substituted alkyl,
  (ii) substituted or unsubstituted, mono- or poly-unsaturated aromatic or heteroaromatic substituents, in particular aryl or heteroaryl, wherein said C-linked substituents comprise from 1 to 6 carbon atoms and from 0 to 5 heteroatoms selected from the group consisting of O, F, N, P and Si;

(b) S-linked substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;

(c) O-linked substituents selected from the group consisting of $OA^1$, $ONA^1A^2$;

(d) N-linked substituents selected from the group consisting of $NA^1A^2$; $(NA^1A^2A^3)^+$, $NA^1SA^2$, $NO_2$; $NA^1A^2$;

(e) halogens selected from the group consisting of F, Cl, Br, and I; and (f) hydrogen;

wherein $A^1$, $A^2$, and $A^3$ are independently selected from the group consisting of hydrogen; substituted or unsubstituted, straight or branched or cyclic, saturated or unsaturated, aliphatic or heteroaliphatic or aromatic or heteroaromatic substituents, preferably substituted or unsubstituted alkyl, or $A^1$ and $A^2$ together with nitrogen atoms to which they are bound form a ring; wherein said substituents or ring comprise from 1 to 6 carbon atoms and from 0 to 5 heteroatoms selected from the group consisting of O, S, N, P, and Si.

Suitable salts of formula (II) are for example chlorides, bromides, sulfates, malates, tartrates, lactates and acetates.

In preferred embodiments, $R_4$, $R_5$, $R_6$, $R_7$ and $R_8$ are independently selected from hydrogen, hydroxyl, C1-C6 alkyl, C2-C6 hydroxyalkyl, amino, C1-C6 alkylamino, C2-C6 hydroxyalkylamino, C1-C6 alkoxy and mixtures thereof. Preferred pyridine derivatives of formula (II) are 3,4-dimethylpyridine-2,6-diol, pyridine-2,6-diamine, 2,6-dimethoxypyridine-3,5-diamine, 6-methoxy-N2-methylpyridine-2,3-diamine, and 2-aminopyridin-3-ol.

In a more preferred embodiment the pyridine derivative (II) is a compound with formula (II.1):

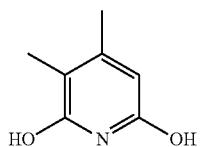

(II.1)

In a preferred embodiment the pyridine derivative (II) is a compound with formula (II.2):

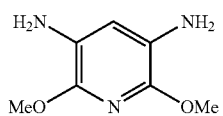

(II.2)

In a preferred embodiment the pyridine derivative (II) is a compound with formula (II.3):

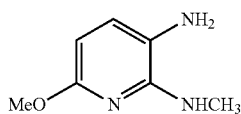

(II.3)

In a preferred embodiment the pyridine derivative (II) is a compound with formula (II.4):

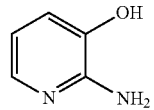

(II.4)

The hair dyeing composition of the present invention further may be comprised of an auxiliary coupler. In a preferred embodiment the auxiliary coupler is a compound with formula (III.1):

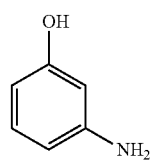

(III.1)

In a preferred embodiment the auxiliary coupler is a compound with formula (III.2):

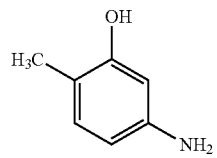

(III.2)

In a preferred embodiment the auxiliary coupler is a compound with formula (III.3):

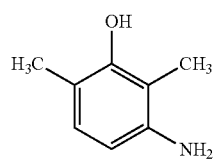

(III.3)

In a preferred embodiment the auxiliary coupler is a compound with formula (III.4):

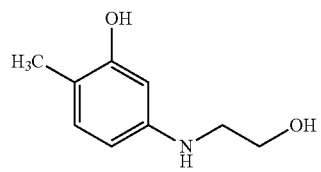

(III.4)

In a preferred embodiment the auxiliary coupler is a compound with formula (III.5):

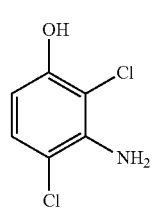

(III.5)

In a preferred embodiment the auxiliary coupler is a compound with formula (III.6):

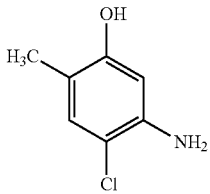

(III.6)

In a preferred embodiment the auxiliary coupler is a compound with formula (III.7):

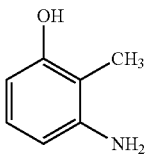

(III.7)

In another preferred embodiment the m-aminophenol compound (III) is a compound with formula (II.8):

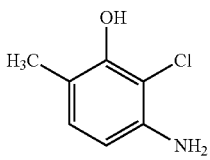

(III.8)

It has surprisingly been found that the modification of the pyrazole ring system in N-1-position by a C6/C7 straight alkyl chain provides a dye precursor which couples with a pyridine compound to give excellent properties of resistance to the various treatments which keratinous fibers may undergo, in particular washfastness and resistance to bleeding.

Oxidizing Agent

The compositions of the invention comprise an oxidizing agent. Typical suitable oxidizing agents for the oxidative dyeing of keratin fibers may be selected from hydrogen peroxide, sodium periodate, urea peroxide, melamine peroxide, perborates, percarbonates, perphosphates, persilicates, persulfates, oxidizing enzymes such as uricases, oxidases, and peroxidises, and mixtures thereof. Hydrogen peroxide, perborates, or percarbonates may be preferred.

Another potential oxidizing agent for use herein is a source of peroxymonocarbonate ions. Preferably, such a source is formed in situ from a source of hydrogen peroxide and a hydrogen carbonate ion source. Such an oxidizing agent has been found to be particularly effective at a pH of up to and including 9.5, preferably from about 7.5 to about 9.5 more preferably about pH 9. Moreover, this system is also particularly effective in combination with a source of ammonia or ammonium ions.

Accordingly, any source of these peroxymonocarbonate ions may be utilized. Suitable sources for use herein include sodium, potassium, guanidine, arginine, lithium, calcium, magnesium, barium or ammonium salts of carbonate, carbamate and hydrocarbonate ions and mixtures thereof. In particular, sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof may be preferred. Percarbonate salts may also be utilized to provide both the source of carbonate ions and as an oxidizing agent. Preferred sources of carbonate ions, carbamate and hydrocarbonate ions are sodium hydrogen carbonate, potassium hydrogen carbonate, ammonium carbonate, ammonium carbamate, and mixtures thereof.

The hair dyeing composition may usually comprise from about 1% to about 15% by total weight of the composition, typically from about 1.5% to about 10% by weight, and more typically from about 2% to about 8% by weight of the oxidizing agent relative to the total weight of the composition.

The oxidizing agent may be provided in a developer component which is mixed to a tint component to obtain the composition of the invention. The developer component may be based on any desired formulation chassis, including any commercial product, for example an oil-in-water emulsion. Typical developer components comprise about 6% or about 9% of $H_2O_2$ by total weight of the composition. A commercial example is the Welloxon® Emulsion with respectively about 6% and about 9% $H_2O_2$, marketed by Wella and comprising as INCI ingredients: Water, Hydrogen Peroxide, Cetearyl Alcohol, Ceteareth-25, Salicylic Acid, Phosphoric Acid, Disodium Phosphate, Etidronic Acid.

The hair dyeing composition of the invention may be formed as thick liquid, cream, gel, emulsion, foam, aerosol mousse or as a solid form to which water is added to generate the oxidant and form a thickened vehicle suitable for hair coloring. They may comprise in addition to the ingredients indicated above further ingredients in order to further enhance the properties of the composition, including but not limited to: solvents; oxidative dyes, direct dyes; oxidizing agents; radical scavengers; thickeners and or rheology modifiers; chelants; pH modifiers and buffering agents; carbonate ion sources; peroxymonocarbonate ion sources; anionic, cationic, nonionic, amphoteric or zwitterionic surfactants, or mixtures thereof; anionic, cationic, nonionic, amphoteric or zwitterionic polymers, or mixtures thereof; fragrances; enzymes; dispersing agents; peroxide stabilizing agents; antioxidants; natural ingredients, e.g. proteins and protein compounds, and plant extracts; conditioning agents including silicones and cationic polymers, ceramides, preserving agents; and opacifiers and pearling agents (such as titanium dioxide and mica). Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose. A few of these ingredients are discussed hereinbelow, whose disclosure is of course non-exhaustive.

Alkalizing Agent

The composition for the oxidative dyeing of keratin fibers may further comprise, generally in the tint component, an alkalizing agent as known in the art. Any alkalizing agent known in the art may be used such as ammonia, alkanolamines for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol, guanidium salts, alkali metal and ammonium hydroxides such as sodium hydroxide, alkali metal and ammonium carbonates, and mixtures thereof. Typical alkalizing agents are ammonia and/or monoethanolamine.

Typically, the compositions for the oxidative dyeing of keratin fibers comprise from about 0.1% to about 10%, preferably from about 0.5% to about 6%, more preferably from about 1% to about 4% by weight of the alkalizing agent relative to the total weight of the composition.

Primary Intermediates

In addition to the pyrazole compounds of the invention, the hair dyeing compositions of the invention may comprise further primary intermediates. Suitable primary intermediates for use in the compositions described herein include, but are not limited to: toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, salts thereof (for example chlorides, bromides, sulfates, malates, tartrates, lactates and acetates) and mixtures thereof.

Of particular interest are toluene-2,5-diamine, p-phenylenediamine, 2-hydroxyethyl-p-phenylenediamine, 2-methoxymethyl-p-phenylenediamine, 2-(2,5-diamino-4-methoxyphenyl)propane-1,3-diol, 2-chloro-p-phenylenediamine, 2-methoxy-p-phenylenediamine, 2-((2-(4-aminophenylamino)-ethyl)-(2-hydroxyethyl)-amino)-ethanol, their salts thereof (for example chlorides, bromides, sulfates, malates, tartrates, lactates and acetates) and combinations.

Typically, the compositions for the oxidative dyeing of keratin fibers comprise from about 0.1% to about 10%, preferably from about 0.3% to about 6%, more preferably from about 0.5% to about 4% by weight of the primary intermediates relative to the total weight of the composition.

Couplers

In addition to the pyridine compounds of the invention, the hair dyeing compositions of the invention may comprise other couplers to obtain various shades. Suitable couplers for use in the compositions described herein include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis (azanediyl)diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]-dioxol-5-ylamino)ethanol (also known as hydroxyethyl-3,4-methylenedioxyaniline), and mixtures thereof.

When the composition is obtained by mixing a tint component and a developer component, additional primary intermediates and couplers may be preferably incorporated in the tint component.

Typically, the compositions for the oxidative dyeing of keratin fibers comprise from about 0.1% to about 10%, preferably from about 0.3% to about 6%, more preferably from about 0.5% to about 4% by weight of the couplers relative to the total weight of the composition.

Direct Dyes

The compositions of the present invention may also comprise compatible direct dyes, in an amount sufficient to provide additional coloring, particularly with regard to intensity. Typically, such an amount will range from about 0.05% to about 4%, by weight of the direct dyes relative to the total weight of the composition. When the composition is obtained by mixing a tint component and a developer component, the direct dyes are usually incorporated in the tint component.

The following direct dyes are commonly used: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4, Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl)(ethyl)amino) ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl) butane-1-sulfonate, N,N-dimethyl-3-(4-(methylamino)-9,10-dioxo-4a,9,9a,10-tetrahydroanthracen-1-ylamino)-N-propylpropan-1-aminium bromide, Disperse Dyes such as Disperse Red 17, Disperse Violet 1, Disperse Red 15, Disperse Violet 1, Disperse Black 9, Disperse Blue 3, Disperse Blue 23, Disperse Blue 377, Nitro Dyes such as 1-(2-(4-nitrophenylamino) ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene) bis(azanediyl)diethanol, HC Yellow No. 5, HC Red No. 7, HC Blue No. 2, HC Yellow No. 4, HC Yellow No. 2, HC Orange No. 1, HC Red No. 1,2-(4-amino-2-chloro-5-nitrophenylamino)ethanol, HC Red No. 3,4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9,2-chloro-6-(ethylamino)-4-nitrophenol, 6-nitropyridine-2,5-diamine, HC Violet No. 2,2-amino-6-chloro-4-nitrophenol, 4-(3-hydroxypropylamino)-3-nitrophenol, HC Yellow No. 13,6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14, and Natural dyes such as Annato, Anthocyanin, Beetroot, Carotene, Capsanthin, Lycopene, Chlorophyll, Henna, Indigo, Cochineal.

Thickeners

The hair dyeing compositions of the present invention may comprise a thickener in an amount sufficient to provide the composition with a viscosity so that it can be readily applied to the hair without unduly dripping off the hair and causing mess. Typically, such an amount will be at least 0.05%, preferably at least 0.5%, more preferably at least 1%, by weight of thickener relative to the total weight of the composition. When the composition is obtained by mixing several components, the thickener may be present in any of the components.

Preferred for use herein are salt tolerant thickeners, including but not limited to: xanthan, guar, hydroxypropyl guar, scleroglucan, methyl cellulose, ethyl cellulose (available as AQUACOTE™), hydroxyethyl cellulose (NATROSOL™), carboxymethyl cellulose, hydroxypropylmethyl cellulose, microcrystalline cellulose, hydroxybutylmethyl cellulose, hydroxypropyl cellulose (available as KLUCEL™), hydroxyethyl ethyl cellulose, cetyl hydroxyethyl cellulose (available as NATROSOL™ Plus 330), N-vinylpyrollidone (available as POVIDONE™), Acrylates/Ceteth-20 Itaconate Copolymer (available as STRUCTURE™ 3001), hydroxypropyl starch phosphate (available as STRUCTURE™ ZEA), polyethoxylated urethanes or polycarbamyl polyglycol ester (e.g. PEG-150/Decyl/SMDI copolymer (available as ACULYN™ 44), PEG-150/Stearyl/SMDI copolymer available as ACULYN™ 46), Acrylates/Beheneth-25 Methacrylate Copolymer (available as ACULYN™ 28), Acrylates/Vinyl Neodecanoate Crosspolymer (available as ACULYN™ 38), Acrylates/Steareth-20 Methacrylate Crosspolymer (available as ACULYN™ 88), PEG-150 Distearate (available as ACULYN™ 60), trihydroxystearin (available as THIXCIN™), acrylates copolymer (e.g. available as ACULYN™ 33) or hydrophobically modified acrylate copolymers (e.g. Acrylates/Steareth-20 Methacrylate Copolymer (available as ACULYN™ 22), non-ionicamphophilic polymers comprising at least one fatty chain and at least one hydrophilic unit selected from polyether urethanes comprising at least one fatty chain.

Also preferred for use herein are thickeners based on lamellar gel network systems, comprising at least one surfactant or amphophile having an HLB of 6 or less and a melting point of at least 30° C., preferably selected from fatty alcohols comprising from 14 to 30 carbon atoms, or oxyethylenated fatty alcohols comprising from 16 to 30 carbon atoms and 2 units or less of ethylene oxide, and further comprising at least one ionic or nonionic surfactant, preferably selected from:

anionic surfactants selected from C8-C30 alkyl sulfates, preferably C12-C18 alkyl sulfates, anionic surfactants according to the formula $R_nX_mYM$, wherein R is independently selected from alkyl, alkenyl or alkylaryl groups having from 8 to 30 carbon atoms, X is independently selected from polar groups comprising at least one carbon atom and at least one oxygen or nitrogen atom, Y is an anionic group selected from carboxylates, sulfates, sulfonates or phosphates, n and m are independently 1 or 2, and M is hydrogen or a salt forming cation and mixture thereof, most preferably selected from C8-C30 alkyl ether phosphates having from 1 to 20, preferable 2 to 10 ethylene oxide units (e.g. available as CRODAFOS™ CES), non-ionic surfactant comprising one or more polyethyleneoxide chains, preferably each polyethyleneoxide chain has on average at least 50 ethylene oxide units and most preferably 100 to 200 ethylene oxide units (e.g. available as VOLPO™ S200), cationic surfactants selected from quaternary ammonium salts or amido-amines having at least one fatty chain, preferably comprising at least 16 carbon atoms and most preferably at least 20 carbon atoms, and mixture thereof.

Examples of such lamellar gel network systems are disclosed in EP1,832,273 and EP2,103,299.

The composition preferably comprises a mixture of cetearyl alcohol and dicetyl phosphate and ceteth-10 phosphate (e.g. available as CRODAFOS™ CES).

Chelants

The compositions of the present invention may comprise chelants in an amount sufficient to reduce the amount of metals available to interact with formulation components, particularly oxidizing agents, more particularly peroxides and percarbonates. Typically, such an amount range from at least 0.15%, preferably at least 0.25%, by weight of the chelants relative to the total weight of the composition. Suitable chelants for use herein include but are not limited to: diethylenetriamine-N,N',N"-polyacids, diethylenetriaminepentaaceticacid (DTPA), diethylenetriaminepenta(methylene phosphonicacid) (DTPMP), diamine-N,N'-dipolyacid, monoamine monoamide-N,N'-dipolyacid, and N,N'-bis(2-hydroxybenzyl)ethylenediamine-N,N'-diaceticacid chelants (preferably EDDS (ethylenediaminedisuccinicacid)), carboxylicacids (preferably aminocarboxylicacids), phosphonicacids (preferably aminophosphonicacids) and polyphosphoricacids (in particular straight polyphosphoricacids), their salts and derivatives. When the composition is obtained by mixing a tint component and a developer component, the chelants may be incorporated in the tint component or in the developer component or in both. A chelant is usually present in developer components for stability reason.

pH Modifiers

The compositions of the present invention may comprise in addition to the alkalizing agent discussed above a pH modifier and/or buffering agent in an amount that is sufficiently effective to adjust the pH of the composition to fall within a range from about 3 to about 13, preferably from about 8 to about 12, more preferably from about 9 to about 11.

Radical Scavengers

According to the present invention, the compositions may comprise a radical scavenger. As used herein the term radical scavenger refers to a species that can react with a radical, to convert the radical species by a series of fast reactions to an unreactive or less reactive species. The radical scavenger is also preferably selected such that it is not an identical species as the alkalising agent and is present in an amount sufficient to reduce the damage to the hair during the coloring/bleaching process. The compositions of the present invention comprise a radical scavenger from about 0.1% to about 10%, preferably from about 1% to about 7% by weight of the radical scavenger relative to the total weight of the composition. Suitable radical scavengers for use herein may be selected from the classes of alkanolamines, amino sugars, amino acids, esters of amino acids and mixtures thereof. Suitable compounds include 3-substituted-pyrazol-5-ones, 3-carboxy-1H-pyrazol-5-one, 3-methyl-1-phenyl-pyrazol-5-one, 3-methyl-1-p-tolyl-pyrazol-5-one, 3-methyl-1-(4-sulfophenyl)-pyrazol-5-one, 3-methyl-1-S(4-sulfoamidophenyl)-pyrazol-5-one, 3-methyl-1-(3-sulfophenyl)-pyrazol-5-one, 3-methyl-1-(3-sulfoamidophenyl)-pyrazol-5-one, 3-methyl-1-(2-chloro-5-sulfophenyl)-pyrazol-5-one, 3-methyl-1-(2,5-dichloro-4-sulfophenyl)-pyrazol-5-one, 3-methyl-1-(4-chlorophenyl)-pyrazol-5-one, 3-methyl-1-(4-carboxyphenyl)-pyrazol-5-one, 3-carboxy-1-phenyl-pyrazol-5-one, 3-carboxy-1-(4-sulfophenyl)-pyrazol-5-one, 1,3-diphenyl-pyrazol-5-one, methylpyrazol-5-one-3-carboxylate, 3-amino-1-propanol, 4-amino-1-butanol,5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamicacid, tryptophan, or mixtures thereof, or the salts, such as the potassium, sodium, or ammonium salts, or mixtures thereof. In some embodiments, the inventive compositions may comprise glycine, sarcosine, lysine, serine, 2-methoxyethylamine, glucosamine, glutamicacid, morpholine, piperidine, ethylamine, 3-amino-1-propanol, or mixtures thereof.

Method of Hair Dyeing

In order to use the dyeing composition, the tint component and developer components are usually mixed immediately prior to use and a sufficient amount of the mixture is applied to the hair, according to the hair abundance, generally from about 60 to about 250 grams. Upon such preparation the composition is applied to the hair to be dyed and remains in contact with the hair for an amount of time effective to dye the hair. Typically, the hair dye composition is allowed to act on the hair from about 2 to about 60, preferably about 15 to about 45, more preferably about 30 minutes, at a temperature ranging from 15° C. to about 50° C. Thereafter, the hair is rinsed with water to remove the composition and dried. If necessary, the hair is washed with a shampoo and rinsed, e.g., with water or a weakly acidic solution, such as a citricacid or tartaricacid solution, and dried. Optionally, a separate conditioning product may also be provided.

The method of dyeing hair with the composition may therefore comprise the steps of:

(i) providing a tint component comprising (a) a 1-hexyl/heptyl-4,5-diaminopyrazole compound of the general formula (I) as defined in claim 1, its physiologically compatible, water-soluble salt, or mixtures thereof and, (b) a pyridine compound of the general formula (II) as defined in claim 1, its physiologically compatible water-soluble salt, or mixtures thereof;

(ii) providing a developer component comprising (c) an oxidizing agent;

(iii) mixing the tint component and the developer component to obtain a composition for the oxidative dyeing of keratin fibers according to the composition of the invention;

(iv) applying said composition for the oxidative dyeing of keratin fibers onto the hair.

The method may further comprise waiting a period of time, typically between 2 minutes and 60 minutes, and then rinsing the composition from the hair.

The compositions can be applied on hair via applicator bottle or brush. It can be used on full head or partly on single strands (highlight application) as common highlight applicator foils, caps and special applicators can be used, but also freehand techniques such as balayage, with brush and/or combs can be possible. The composition can also be applied as a mousse via a manual spray, a pressurized container or an aerosol mousse.

The composition may be dispensed as a solid form to which water is added to generate the oxidant and form a thickened vehicle suitable for hair coloring.

The dye combination of the invention may also be used in three components system. See for example disclosed US2010/0223739A2 assigned to L'Oreal. Such a process and kit for lightening or dyeing keratin fibers may comprise the following composition applied to the hair fibers: an aqueous cosmetic composition (A) comprising at least one fatty substance and at least one surfactant; a cosmetic composition (B) comprising at least one alkaline agent and the oxidative dyes of the invention and if present direct dyes and other oxidative dyes, a cosmetic composition (C) comprising at least one oxidizing agent, wherein the amount of the at least one fatty substance in composition (A) is greater than 20% by weight relative to the total weight of composition (A).

Methods of Making—Kit

The composition, and its tint component and developer component, may be manufactured by conventional processes known in the art for manufacturing oxidative dyeing products, and ad-mixing the ingredients of each component composition in suitable vessels, followed by packaging in appropriate individual containers. The components may be for example packaged in plastic or aluminium bottles.

In particular, the present invention may be provided as a kit comprising different components to be mixed by the consumer or salon stylist to obtain a hair dyeing composition according to the invention. Such a kit may comprise:

(i) a tint component comprising (a) a 1-hexyl/heptyl-4,5-diaminopyrazole compound of the general formula (I) as defined above, its physiologically compatible water-soluble salt, or mixtures thereof, and (b) a pyridine compound of the general formula (II) as defined above, its physiologically compatible water-soluble salt, or mixtures thereof, and ii) a developer component comprising an oxidizing agent.

The kit may be presented in a single package comprising separate containers for the tint component, the developer component, and optionally a conditioner, a color refresher or other hair treatment product, instructions for use, gloves. The instructions for use include the steps of the method described above and optionally provide visual cues or pictures for the desired steps of the method. Kits are usually sold in retail products with enough material in each component for preparing a hair dyeing composition for one use.

The composition may be dispensed as a foam using for example manually-actuable, non-aerosol dispenser such as a pump or squeeze foamer, aerosol mousse. See for example EP 613,728 B1, WO 97/013585 A1, EP 1,716,933A1, U.S. Pat. Nos. 3,709,437, 3,937,364, 4,022,351, 4,147,306, 4,184,615, 4,615,467 and FR 2,604,622. One particular example of a squeeze foamer useful herein is able to dispense from an upright or inverted position such as the one discussed in U.S. Pat. No. 6,604,693 assigned to Taplast, and more specifically, at column 2, line 65, through column 4, line 67 of that patent.

The composition may be dispensed as a solid form to which water is added to generate the oxidant and form a thickened vehicle suitable for hair coloring

EXAMPLES

The following are non-limiting examples of the compositions of the present invention. The examples are given solely for the purpose of illustration and are not to be construed as limitations of the present invention, as many variations thereof are possible without departing from the spirit and scope of the invention, which would be recognized by one of ordinary skill in the art. All concentrations are listed as weight percent, unless otherwise specified.

The compositions tested were formulated by mixing a tint component according to the formulation below with a developer component in a 1:1 ratio. The developer component is a commercially available Welloxon developer at 6% (20 vol) peroxide concentration. In all the tests, white hair was used (1.5 g tress). 3 g tint component +3 g developer component were applied for each switch for 30 minutes at 30° C. The tresses were rinsed for 2 minutes including 30 seconds shampoo.

TABLE 1

Tint Formulation:

| Ingredients | Weight % |
| --- | --- |
| Lanolin alcohol | 2.0 |
| Glyceryl Stearate | 5.5 |
| Glycol Distearate | 2.0 |
| Cetearyl alcohol and SLS | 17.5 |
| Sodium cocoyl isethionate | 0.46 |
| Sodium laureth sulfate | 4.0 |
| Ascorbic acid | 0.3 |
| Sodium sulfate | 0.001 |
| Sodium sulfite | 0.4 |
| Disodium EDTA | 0.1 |
| Alkyl (C5, C6 or C8) Pyrazole salts (%) | X |
| Coupler (%) | Y |
| Ammonia, 28.3% in water | 6.43 |
| Fragrance | 0.25 |
| Reverse osmosis water | QS to 100% |
| | Total Wt |

X and Y were calculated dependent upon the alkyl pyrazole and coupler type to reach a final molar concentration of ca. 0.075 M in the tint component formulation.

Color Intensity

After mixing with the tint component indicated with the developer component, the resulting mixture was applied to white hair and rinsed. The resulting color was measured using a colorimeter and characterized by the L* value. An L* of 100 is considered white and L* of 0 is considered black, therefore the higher the L* value the lower the color intensity. The measured L* values for the different primary dye combinations are summarized in Table 2 below.

TABLE 2

Comparison of L* values

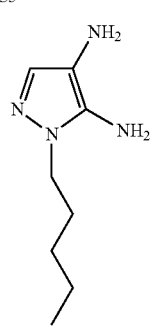

(II.2)

| | |
| --- | --- |
| C5 | 16.35 |
| C6 | 16.44 |
| C8 | 18.18 |

Table 2 demonstrates that the L* values of hair tresses dyed with the C8 alkyldiaminopyrazole combined with 2,6-dimethoxypyridine-3,5-diamine are significantly higher compared to the other alkyldiaminopyrazoles with 2,6-dimethoxypyridine-3,5-diamine. As the C8 alkyldiaminopyrazole combined with 2,6-dimethoxypyridine-3,5-diamine clearly does not give the desired color intensity, it will not be further analyzed or compared to the present invention.

Table 2 demonstrates that the L* values of hair tresses dyed with the c8 alkyldiaminopyrazole combined with 2,6-dimethoxypyridine-3,5-diamine are significantly higher compared to the other alkyldiaminopyrazoles with 2,6-dimethoxypyridine-3,5-diamine. As the C8 alkyldiaminopyrazole combined with 2,6-dimethoxypyridine-3,5-diamine clearly does not give the desired color intensity, it will not be further analyzed or compared to the present invention.

Wash Fade Test

The wash fade measures the fading of the color after repeated wash cycles (up to 24). In this test, five hair tresses are dyed and the initial color measurements are obtained, one is retained for reference. Shampoo is then applied according to this procedure. The four remaining hair tresses are thoroughly wet for 30 sec. 0.1 g of a conventional shampoo per gram of hair (e.g. 0.1 g shampoo for each 1.0 g tress) is applied. The shampoo is applied with a syringe using a zigzag action down the length of the hair. The shampoo is milked into hair for 30 secs, ensuring even application, at a speed of less than 30 strokes/60 seconds (for example—1 stroke every 2 seconds) using a '2 fingers and thumb' action.

The shampoo is then rinsed according to this procedure: the rinse water temperature is set to 37° C.±1° C. and flowrate to 4±0.5 l/min. The sprayer is held at an angle to the tresses and the tresses are rinsed for 30 seconds while gently stroking the shampoo out of the hair (20 strokes total). Multiple tresses may be rinsed at the same time, as long as water is running over all tresses. A total time of 30 seconds and a total of 20 strokes should be used for multiple tresses. After rinsing, starting at the top of the tress, the tress is squeezed between fingers to remove excess water (one stroke).

The tresses are then dried according to the procedure: the tresses are laid onto a clean paper towel and blotted gently. The tresses are held 10 cm from a blow dryer (set to high heat) and dried 1.5 min while using fingers to separate the hair. If needed, the hair is brushed gently twice. The tresses are turned over and dried 1.5 min while using fingers to separate the hair. If needed, hair is brushed gently twice. Between washings, hair tresses are kept out of light; either wrapped in aluminum foil or stored in a drawer.

This procedure is repeated on the remaining four hair tresses for each dye sample. Color readings are taken at the $3^{rd}$, $6^{th}$, $9^{th}$, $12^{th}$, $15^{th}$, $18^{th}$, $21^{st}$ and $24^{th}$ shampoo/rinse/dry cycle washing intervals. At the $6^{th}$, $12^{th}$, $18^{th}$ and $24^{th}$ shampoo/rinse/dry cycle one hair tress was retained for color measurements and visual assessments.

For the present experiment, C5 and C6 alkyldiaminopyrazoles were tested in combination with a pyridine derivative of formula (II.2):

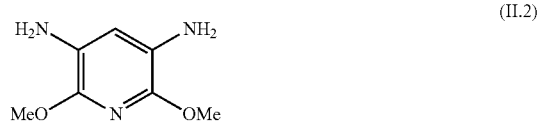 [SMILES: COc1nc(OC)c(N)cc1N]

The starting value (0 wash cycle) for each combination of dyes was taken as a reference and the delta $\Delta E^* = \sqrt{((\Delta L^*)^2 + (\Delta a^*)^2 + (\Delta b^*)^2)}$ values were calculated for each cycle relative to it $\Delta E_x^* = \sqrt{((L_x^* - L_0^*)^2 + (a_x^* - a_0^*)^2 + (b_x^* - b_0^*)^2)}$. The results are summarized in the Table 4 below:

TABLE 3

Wash fade testing result.

| Cycle | C6 | C5 |
|---|---|---|
| 0 | 0 | 0 |
| 6 | 1.33 | 1.41 |
| 12 | 1.33 | 1.59 |
| 18 | 1.97 | 2.30 |
| 24 | 1.63 | 3.90 |

As can be seen on Table 3, this experiment demonstrates a higher rate of loss of color from hair tresses dyed in the following order C5>C6.

Diffusion Testing

The diffusion testing protocol measures the ability for the dye to stay within the hair when the fibers are wet. In this test, dyed tresses of hair were prepared as indicated above and then separately immersed in a 1 liter beaker containing 900.0 g water. The beaker was placed in the center of a stir plate and the tress attached to a clamping device that was used to lower the tress into the beaker. When in the beaker, the tress remained above the stir bar in the center of the beaker. The tress was lowered until the water line was at the top of the hair tress. The stir plate was turned on so that the stir bar would spin at approximately 100 rpm. All tresses were tested at the same spin rate. The tress was left in the beaker with stir bar rotating for three hours. After the three hours, the tresses were removed. The absorbance spectrum of the remaining solution was measured using a UV-vis spectrophotometer to characterize the amount of dye that diffused out of the hair into the solution. A full absorbance spectrum from 400 to 700 nm was measured and the absorbance at the peak maximum was measured for each case. The absorbance values for the C5 and C6 alkyldiaminopyrazole combinations are normalized and account for differences in starting dye concentrations in the hair fibers.

FIG. 1 demonstrates the rate of increase of absorbance values after following the diffusion testing protocol with hair tresses dyed with the indicated combination of C5 or C6 alkyldiaminopyrazole with 2,6-dimethoxypyridine-3,5-diamine.

1. ♦ a C5 alkyl diamino pyrazole in combination with 2,6-dimethoxypyridine-3,5-diamine.
2. ■ a C6 alkyl diamino pyrazole in combination with 2,6-dimethoxypyridine-3,5-diamine.

Equations for Lines on Graph:

$C5 y = 6E-05x + 0.0081$ $C6 y = 3E-05x + 0.004$

The C6 alkyldiaminopyrazole consistently leaches less dye materials into solution than the C5 alkyldiaminopyrazole. This implies that less color diffuses from the hair tresses containing the C6 relative to the C5 alkyldiaminopyrazole.

Towel Bleeding

A consumer relevant measure of the ability to see differences in washfastness is to assess how much color from wet dyed hair tresses transfers to a white cloth, such as a white wash cloth. The amounts of towel bleeding resulting from washed tresses dyed with a C5 alkyldiaminopyrazole and C6 alkyldiaminopyrazole with compound of formula (II.1) were measured using conventional $\Delta E^*$ measurements. The testing method is summarized below:

After washing a dyed hair switch by the method described above, place the switch on a white cloth (50% cotton, 50% polyester) with an average color reading of $L^*=95.8$, $a^*=-1.40$ and $b^*=0.89$. Fold the cloth in half over the hair switches. Place a 2.27 kg weight on the folded cloth for 5 min. Upon removal of the hair, visual inspection shows a larger and more intense stain for the C5 alkyldiaminopyrazole compared to the C6 alkyldiaminopyrazole compound. The noticeability of the stain on the fabric was calculated using the $\Delta E$ measurements for C5 and C6 relative to the fabric. (see $\Delta E^*$ values below). A higher $\Delta E^*$ value shows more color transfer to the cloth (bleeding).

TABLE 4

Towel bleeding results

| | C5 | C6 |
|---|---|---|
| (II.2) | $\Delta E = 3.66$ | $\Delta E = 2.94$ |

It was found that the C6 alkyldiaminopyrazole dye had a stain intensity of almost 50% less noticeable than the C5 alkyldiaminopyrazole dye after one wash cycle.

Additional Examples

The Color Intensity, Diffusion Testing, and Towel Bleeding test as indicated above were conducted under the same conditions with a tint component comprising 2,5-toluenediamine sulfate (DTS) as a further primary intermediate as indicated in Table 5 below.

TABLE 5

Tint Formulation with DTS

| Ingredients | Weight % |
|---|---|
| Lanolin alcohol | 2.0 |
| Glyceryl stearate | 5.5 |
| Glycol Distearate | 2.0 |
| Cetearyl alcohol and SLS (9:1) | 17.5 |
| Sodium cocoyl isethionate | 0.46 |
| Sodium laureth sulfate | 4.0 |
| Ascorbic acid | 0.3 |
| Sodium sulfate | 0.001 |
| Sodium sulfite | 0.4 |
| Disodium EDTA | 0.1 |
| Sodium chloride | 0.292 |
| C5 pyrazole salt | 0.869 |
| Or | Or |

TABLE 5-continued

Tint Formulation with DTS

| Ingredients | Weight % |
|---|---|
| C6 pyrazole salt | 0.925 |
| Or | Or |
| C8 Pyrazole salt | 1.042 |
| 2,6-dimethoxypyridine-3,5-diamine | 1.211 |
| 2,5-toluenediamine sulfate (DTS) | 0.220 |
| Ammonia, 28.3% in water | 6.43 |
| Fragrance | 0.25 |
| Reverse osmosis water | QS to 100% Total Wt |

The combined amount of pyrazole and DTS represents a total molar concentration of about 0.050M for these primary intermediates.

The results are as indicated below.

Color Intensity

TABLE 6

Comparison of L* values with DTS

| | | |
|---|---|---|
| | (II.2) | •H$_2$SO$_4$ |
| C5 | 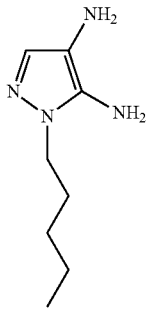 | 17.43 |
| C6 | 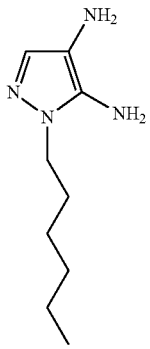 | 17.54 |

TABLE 6-continued

Comparison of L* values with DTS

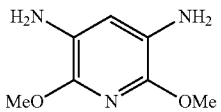

| | |
|---|---|
| C8 | 18.99 |

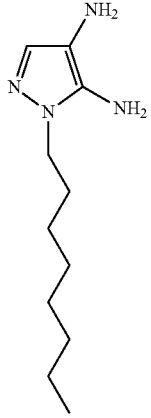

Table 6 demonstrates that the L* values of hair tresses dyed with the C8 alkyldiaminopyrazole combined with 2,5-toluenediamine and 2,6-dimethoxypyridine-3,5-diamine are significantly higher compared to the other alkyldiaminopyrazoles with 2,5-toluenediamine and 2,6-dimethoxypyridine-3,5-diamine.

Diffusion Testing

Figure 2:
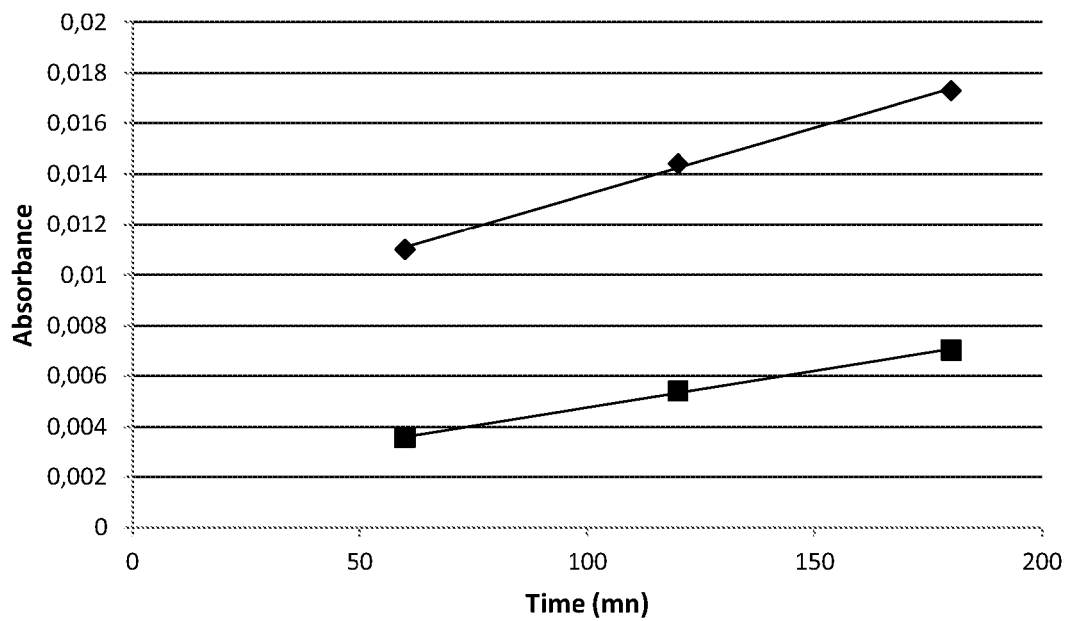
FIG. 2 shows a graph demonstrating the Solution Diffusion Testing results of a 1-pentyl- and 1-hexyl-4,5-diamino pyrazole with 2,6-dimethoxypyridine-3,5-diamine and 2,5-toluenediamine sulfate (DTS).

The same testing as described above was performed and results shown in FIG. 2 for:

1. ♦ a C5 alkyl diamino pyrazole in combination with 2,6-dimethoxypyridine-3,5-diamine and DTS.
2. ■ a C6 alkyl diamino pyrazole in combination with 2,6-dimethoxypyridine-3,5-diamine and DTS, Equations for Lines on Graph $$C5 y = 5E{-}05x + 0.0079$$

$$C6 y = 3E{-}05x + 0.0019$$

Towel Bleeding

TABLE 7

Towel bleeding results

| | C5 | C6 |
|---|---|---|
| 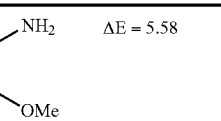 (II.2) | ΔE = 5.58 | ΔE = 3.46 |

Concluding Remark

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition for the oxidative dyeing of keratin fibers, in particular human keratin fibers, comprising:
    (A) a 1-hexyl/heptyl-4,5-diamino pyrazole compound of the general formula (I), a physiologically compatible water-soluble salt thereof, or mixtures thereof,

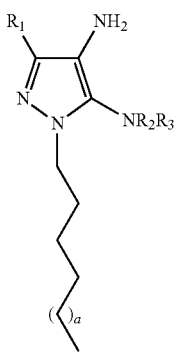

wherein a is equal to one or two;
wherein $R_1$ is selected from the group consisting of:
(a) C-linked substituents selected from the group consisting of:
  (i) substituted or unsubstituted, straight or branched or cyclic, saturated or unsaturated, aliphatic or heteroaliphatic substituents, in particular alkyl or hydroxy substituted alkyl, and
  (ii) substituted or unsubstituted, mono- or poly-unsaturated aromatic or heteroaromatic substituents, in particular aryl or heteroaryl,
  wherein said C-linked substituents comprise from 1 to 6 carbon atoms and from 0 to 5 heteroatoms selected from the group consisting of O, F, N, P and Si;
(b) S-linked substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
(c) O-linked substituents selected from the group consisting of $OA^1$ and $ONA^1A^2$;
(d) N-linked substituents selected from the group consisting of $NA^1A^2$; $(NA^1A^2A^3)^+$, $NA^1SA^2$, $NO_2$; and $NA^1A^2$;
(e) halogens selected from the group consisting of F, Cl, Br, and I; and
(f) hydrogen;
wherein $A^1$, $A^2$, and $A^3$ are selected independently of each other from the group consisting of hydrogen; substituted or unsubstituted, straight or branched or cyclic, saturated or unsaturated, aliphatic or heteroaliphatic or aromatic or heteroaromatic substituents, or $A^1$ and $A^2$ together with nitrogen atoms to which they are bound form a ring; wherein said substituents or ring comprise from 1 to 6 carbon atoms and from 0 to 5 heteroatoms selected from the group consisting of O, S, N, P, and Si;
$R_2$ and $R_3$ are selected independently of each other from the group consisting of a hydrogen atom; a C1-C6 alkyl substituent; a trifluoromethyl substituent; a C1-C6 aminoalkyl substituent; a C1-C6 hydroxyalkyl substituent; and a C1-C6 alkoxyalkyl substituent;
(B) a pyridine compound of the general formula (II), a physiologically compatible water-soluble salt thereof, or mixtures thereof,

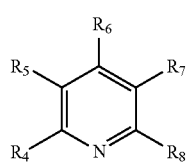

wherein $R_4$, $R_5$, $R_6$, $R_7$ and $R_8$ are substituents selected independently of each other from the group consisting of:
(a) C-linked substituents selected from the group consisting of:
  (i) substituted or unsubstituted, straight or branched or cyclic, saturated or unsaturated, aliphatic or heteroaliphatic substituents, in particular alkyl or hydroxy substituted alkyl, and
  (ii) substituted or unsubstituted, mono- or poly-unsaturated aromatic or heteroaromatic substituents, in particular aryl or heteroaryl,
  wherein said C-linked substituents comprise from 1 to 6 carbon atoms and from 0 to 5 heteroatoms selected from the group consisting of O, F, N, P and Si;
(b) S-linked substituents selected from the group consisting of $SA^1$, $SO_2A^1$, $SO_3A^1$, $SSA^1$, $SOA^1$, $SO_2NA^1A^2$, $SNA^1A^2$, and $SONA^1A^2$;
(c) O-linked substituents selected from the group consisting of $OA^1$ and $ONA^1A^2$;
(d) N-linked substituents selected from the group consisting of $NA^1A^2$; $(NA^1A^2A^3)^+$, $NA^1SA^2$, $NO_2$; and $NA^1A^2$;
(e) halogens selected from the group consisting of F, Cl, Br, and I; and
(f) hydrogen;
wherein $A^1$, $A^2$, and $A^3$ are selected independently of each other from the group consisting of hydrogen; substituted or unsubstituted, straight or branched or cyclic, saturated or unsaturated, aliphatic or heteroaliphatic or aromatic or heteroaromatic substituents, or $A^1$ and $A^2$ together with nitrogen atoms to which they are bound form a ring; wherein said substituents or ring comprise from 1 to 6 carbon atoms and from 0 to 5 heteroatoms selected from the group consisting of O, S, N, P, and Si; and
(C) an oxidizing agent.

2. A composition according to claim 1, wherein the 1-hexyl/heptyl-4,5-diamino pyrazole compound (I) is a compound with formula (I.1):

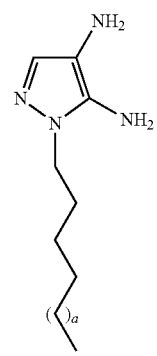

3. A composition according to claim 1, wherein the pyridine compound (II) is selected from the group consisting of compounds with formula (II.1) to (II.4) and combinations thereof:

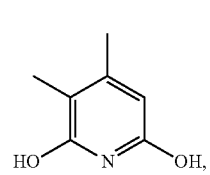

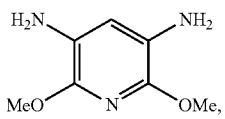
(II.2)

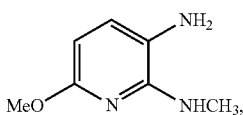
(II.3)

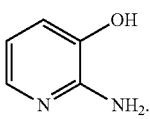
(II.4)

4. A composition according to claim 3 wherein the pyridine compound has the formula (II.2):

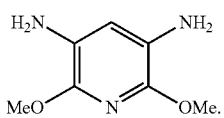
(II.2)

5. A composition according to claim 1 further comprising an auxiliary coupler.

6. A composition according to claim 5, wherein said auxiliary coupler is an aminophenol compound selected from the group consisting of:

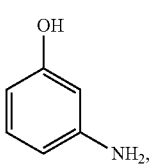
(III.1)

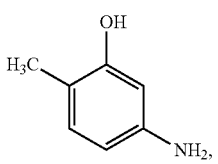
(III.2)

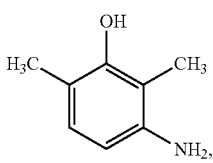
(III.3)

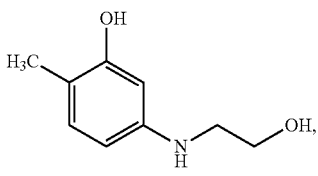
(III.4)

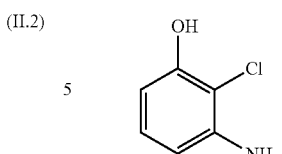
(III.5)

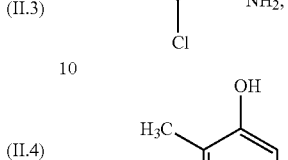
(III.6)

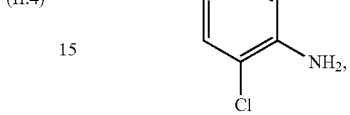
(III.7)

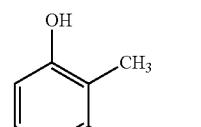

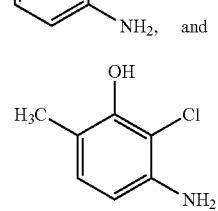
(III.8)

and combinations thereof.

7. A composition according to claim 1, further comprising a primary intermediate selected from the group consisting of toluene-2,5-diamine, p-phenylenediamine, 2-hydroxyethyl-p-phenylenediamine, 2-methoxymethyl-p-phenylenediamine, 2-(2,5-diamino-4-methoxyphenyl)propane-1,3-diol, 2-chloro-p-phenylenediamine, 2-methoxy-p-phenylenediamine, 2-((2-(4-amino-phenylamino)-ethyl)-(2-hydroxy-ethyl)-amino)-ethanol, salts thereof and combination thereof.

8. A composition according to claim 1 further comprising at least one additional component selected from the group consisting of alkalizing agents, auxiliary primary intermediates, auxiliary couplers, direct dyes, thickeners, chelants, pH modifiers and/or buffering agents, radical scavenger systems and mixtures thereof.

9. A composition according to claim 1, further comprising fatty alcohols comprising from 14 to 30 carbon atoms, or oxyethylenated fatty alcohols comprising from 16 to 30 carbon atoms and 2 units or less of ethylene oxide.

10. A composition according to claim 9, further comprising at least one ionic or nonionic surfactant selected from:
anionic surfactants selected from C8-C30 alkyl sulfates;
anionic surfactants according to the formula $R_nX_mYM$, wherein R is independently selected from alkyl, alkenyl or alkylaryl groups having from 8 to 30 carbon atoms, X is independently selected from polar groups comprising at least one carbon atom and at least one oxygen or nitrogen atom, Y is an anionic group selected from carboxylates, sulfates, sulfonates or phosphates, n and m are independently 1 or 2, and M is hydrogen or a salt forming cation and mixture thereof;
non-ionic surfactant comprising one or more polyethyleneoxide chains;
cationic surfactants selected from quaternary ammonium salts or amido-amines having at least one fatty chain; and
mixtures thereof.

11. A composition according to claim 10 comprising a mixture of cetearyl alcohol and dicetyl phosphate and ceteth-10 phosphate.

12. A composition according to claim 1 further comprising a chelant selected from the group consisting of: diethylenetriamine-N,N',N''-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, and N,N'-bis(2-hydroxybenzyl)ethylenediamine-N,N'-diacetic acid chelants, carboxylic acids, phosphonic acids and polyphosphoric acids, their salts and derivatives.

13. A composition according to claim 1 wherein said oxidizing agent is selected from the group consisting of hydrogen peroxide, sodium periodate, urea peroxide, melamine peroxide, perborates, percarbonates, perphosphates, persilicates, persulfates, oxidizing enzymes such as uricases, oxidases, and peroxidases, a source of peroxymonocarbonate ions and mixtures thereof.

14. A composition according to claim 1, wherein said composition is dispensed as a foam.

15. A method of dyeing hair comprising the steps of:
(i) providing a tint component comprising (a) a 1-hexyl/heptyl-4,5-diaminopyrazole compound of the general formula (I) as defined in claim 1, a physiologically compatible water-soluble salt thereof or mixtures thereof and, (b) a pyridine compound of the general formula (II) as defined in claim 1, a physiologically compatible water-soluble salt thereof or mixtures thereof;
(ii) providing a developer component comprising (c) an oxidizing agent;
(iii) mixing the tint component and the developer component to obtain a composition for the oxidative dyeing of keratin fibers according to any of the preceding claims; and
(iv) applying said composition for the oxidative dyeing of keratin fibers onto the hair.

16. An oxidative hair dyeing kit comprising: (i) a tint component comprising (a) a 1-hexyl/heptyl-4,5-diamino pyrazole compound of the general formula (I) as defined in claim 1, a physiologically compatible water-soluble salt thereof or mixtures thereof and,
(b) a pyridine compound of the general formula (II) as defined in claim 1, a physiologically compatible water-soluble salt thereof or mixtures thereof, and ii) a developer component comprising an oxidizing agent.

17. A tint component comprising (a) a 1-hexyl/heptyl-4,5-diaminopyrazole compound of the general formula (I) as defined in claim 1, a physiologically compatible, water-soluble salt thereof or mixtures thereof; and (b) a pyridine compound of the general formula (II) as defined in claim 1, a physiologically compatible water-soluble salt thereof or mixtures thereof.

* * * * *